(12) United States Patent
Abdelmonem

(10) Patent No.: US 6,711,394 B2
(45) Date of Patent: Mar. 23, 2004

(54) RF RECEIVER HAVING CASCADED FILTERS AND AN INTERMEDIATE AMPLIFIER STAGE

(75) Inventor: Amr Abdelmonem, Arlington Heights, IL (US)

(73) Assignee: ISCO International, Inc., Mount Prospect, IL (US)

( * ) Notice: Subject to any disclaimer, the term of this patent is extended or adjusted under 35 U.S.C. 154(b) by 0 days.

(21) Appl. No.: 09/130,274

(22) Filed: Aug. 6, 1998

(65) Prior Publication Data

US 2001/0055960 A1 Dec. 27, 2001

(51) Int. Cl.$^7$ .................................................. H04B 1/18
(52) U.S. Cl. ........................................ 455/307; 455/339
(58) Field of Search ................................ 455/307, 338, 455/339, 286, 280, 283, 207, 561, 191.2; 330/303, 306

(56) References Cited

U.S. PATENT DOCUMENTS

| | | | |
|---|---|---|---|
| 3,629,706 A | * 12/1971 | Chasek | 325/9 |
| 3,737,799 A | 6/1973 | Ständer | 330/126 |
| 3,911,366 A | 10/1975 | Baghdady | 325/347 |
| 3,988,679 A | 10/1976 | Clarke et al. | 325/377 |
| 4,313,223 A | * 1/1982 | Sakamoto | 455/323 |
| 4,406,019 A | * 9/1983 | Ide | 455/245 |
| 4,476,575 A | 10/1984 | Franke et al. | 455/76 |
| 4,609,892 A | 9/1986 | Higgins, Jr. | 333/204 |
| 4,668,920 A | 5/1987 | Jones | 330/286 |
| 4,679,248 A | 7/1987 | McKeown | 455/226 |
| 4,733,403 A | 3/1988 | Simone | 375/103 |
| 4,742,561 A | 5/1988 | Tipton | 455/67 |
| 4,903,257 A | 2/1990 | Takeda et al. | 370/29 |
| 4,907,291 A | 3/1990 | Yamamoto | 455/78 |
| 4,922,509 A | 5/1990 | Tresset et al. | 375/103 |
| 4,972,455 A | 11/1990 | Phillips et al. | 379/59 |
| 5,020,148 A | 5/1991 | Bonato | 455/302 |
| 5,042,085 A | * 8/1991 | Errico | 455/43 |
| 5,083,236 A | 1/1992 | Chason et al. | 361/401 |
| 5,157,364 A | 10/1992 | Pond et al. | 333/203 |
| 5,222,144 A | 6/1993 | Whikehart | 381/15 |

(List continued on next page.)

FOREIGN PATENT DOCUMENTS

| | | |
|---|---|---|
| EP | 0 181 807 A1 | 5/1986 |
| EP | 0 720 248 | 7/1996 |
| GB | 2 235 828 A | 3/1991 |
| JP | 17701 | 1/1990 |
| JP | 10224110 | 8/1998 |
| JP | 10224269 | 8/1998 |
| WO | WO 96/42118 | 12/1996 |

OTHER PUBLICATIONS

Communication Relating to the Results of the Parital International Search, International Application No.: PCT/US 99/21184.

Horowitz, et al., *The Art of Electronics*, Cambridge University Press, 2d ed., pp. 35–42, 263–272 (1989).

Communication Pursuant to Article 96(2) EPC dated Jul. 24, 2003.

*Primary Examiner*—Thanh Cong Le
*Assistant Examiner*—Nick Corsaro
(74) *Attorney, Agent, or Firm*—Marshall, Gerstein & Borun LLP (57) ABSTRACT

An RF receiver includes first and second RF filter stages and an amplifier stage. An output terminal of the first RF filter stage is coupled to an input terminal of the amplifier stage, and an output terminal of the amplifier stage is coupled to an input terminal of the second RF filter stage. The first and second RF filter stages are not identical, inasmuch as, for instance, the first and second RF filter stages may provide different selectivities. The first RF filter stage may include a low loss RF filter to establish a low noise figure for the RF receiver. The isolation provided by the amplifier stage permits the first and second RF filter stages to include high-order RF filters or, alternatively, multiple low order RF filters.

34 Claims, 3 Drawing Sheets

U.S. PATENT DOCUMENTS

| | | | |
|---|---|---|---|
| 5,244,869 A | * 9/1993 | Billing | 505/1 |
| 5,276,914 A | * 1/1994 | Ishizuka | 455/83 |
| 5,324,713 A | 6/1994 | Shen | 505/210 |
| 5,339,459 A | 8/1994 | Schiltz et al. | 455/333 |
| 5,355,524 A | 10/1994 | Higgins, Jr. | 455/82 |
| 5,357,544 A | 10/1994 | Horner et al. | 375/94 |
| 5,412,339 A | * 5/1995 | Takano | 330/54 |
| 5,483,694 A | * 1/1996 | Bartels | 455/295 |
| 5,490,173 A | 2/1996 | Whikehart et al. | 375/316 |
| 5,493,581 A | 2/1996 | Young et al. | 375/350 |
| 5,537,680 A | 7/1996 | Bruno | 455/15 |
| 5,604,925 A | 2/1997 | O'Malley et al. | 455/254 |
| 5,616,540 A | 4/1997 | Lithgow et al. | 505/210 |
| 5,629,266 A | 5/1997 | Lithgow et al. | 505/210 |
| 5,640,698 A | * 6/1997 | Shen | 455/323 |
| 5,697,087 A | 12/1997 | Miya et al. | 455/307 |
| 5,731,841 A | * 3/1998 | Rosenbaum | 348/463 |
| 5,789,347 A | 8/1998 | Button et al. | 505/450 |
| 5,804,534 A | 9/1998 | Zaki | 505/210 |
| 5,930,686 A | * 7/1999 | Devlin | 455/84 |
| 5,963,856 A | * 10/1999 | Kim | 455/307 |
| 6,011,770 A | * 1/2000 | Tan | 369/124 |
| 6,011,983 A | * 1/2000 | Ishikawa | 505/210 |
| 6,014,571 A | * 1/2000 | Enoki | 455/550 |
| 6,112,070 A | * 8/2000 | Katsuyama | 455/307 |
| 6,205,340 B1 | * 3/2001 | Yandrofski | 455/561 |
| 6,212,404 B1 | 4/2001 | Hershtig | 455/561 |

* cited by examiner

RF RECEIVER HAVING CASCADED FILTERS AND AN INTERMEDIATE AMPLIFIER STAGE

FIELD OF THE INVENTION

The present invention relates generally to radio frequency communication systems and, more particularly, to receiver configurations therefor.

BACKGROUND ART

Radio frequency (RF) receivers for cellular telephone base stations and other telecommunication system components must provide high degrees of both selectivity (the ability to distinguish between signals separated by small frequency differences) and sensitivity (the ability to receive weak signals). Typically, an incoming RF signal is first passed through a low loss, passive, RF bandpass filter to remove signal components outside of the frequency range of the desired signal. The resulting filtered signal is then usually amplified by an amplifier that does not introduce a significant amount of noise (i.e., a low noise amplifier or LNA). In this manner, the LNA and other system components are protected from any amplified, undesired signals.

The advent of widespread cellular telephone communication systems has increased the demands placed on these RF filter-amplifier configurations. Selectivity has been increased by using two identical RF bandpass filters instead of relying on a single filter. See U.S. Pat. Nos. 5,537,680, 5,412,339, and 5,355,524. Additional selectivity has also been realized by manufacturing filters having more sections, which add more poles (i.e., frequencies at which the transfer function of a filter approaches unity (0 dB) and the reflection coefficient approaches zero). However, adding another filter or more sections comes at the expense of increased losses (i.e., decreased sensitivity) and, therefore, increased attenuation of potentially very weak incoming signals.

RF filters have been designed such that each additional section introduces very little signal loss. For example, RF filters have included resonant elements utilizing high temperature superconducting (HTSC) materials. HTSC filters have been shown to provide quality factors (Q, the ratio of the center frequency to the 3 dB bandwidth) as high as 100,000. In general, however, low loss filters have a quality factor above about 12,000 and preferably above about 20,000. With each additional pole of an HTSC filter introducing negligible losses, demands for still further rejection have resulted in filter designs having more and more poles. HTSC filters, however, are costly relative to RF filters utilizing conventional materials, as HTSC materials are relatively costly to manufacture and must be maintained at very low temperatures.

While high-order (e.g., sixteen poles) HTSC filters have been manufactured, filters with more than about sixteen sections—whether HTSC or conventional filters—become impractical for several reasons, including the feasibility of manufacturing and tuning them. In general, tuning a filter requires adjustment of both the resonant frequency of each resonant section and the degree and type of electromagnetic coupling between sections. Tuning these high-order filters is problematic because the filter's response becomes highly sensitive to even minor changes in component parameter values.

SUMMARY OF THE INVENTION

In accordance with one aspect of the present invention, an RF receiver includes a first RF filter stage, an amplifier stage, and a second RF filter stage having a different selectivity than the first filter stage. An output terminal of the first RF filter stage is coupled to an input terminal of the amplifier stage, while an output terminal of the amplifier stage is coupled to an input terminal of the second RF filter stage.

The second RF filter stage may provide more rejection than the first RF filter stage, which may include a low loss RF filter. The low loss RF filter of the first RF filter stage may rely on superconducting resonant elements. In contrast, the second RF filter stage may include conventional resonant elements.

According to another aspect of the present invention, an RF receiver includes a first RF filter stage, an amplifier stage, and a second RF filter stage. An output terminal of the first RF filter stage is coupled to an input terminal of the amplifier stage, while an output terminal of the amplifier stage is coupled to an input terminal of the second RF filter stage. The first RF filter stage includes a low loss RF filter, and the second RF filter stage includes an RF filter having a higher insertion loss than the low loss RF filter.

According to yet another aspect of the present invention, an RF receiver includes a first RF filter stage including superconducting material and having an output terminal. The RF receiver further includes an amplifier having an input terminal coupled to the output terminal of the first RF filter stage. The RF receiver still further includes a second RF filter stage including superconducting material and having an input terminal coupled to an output terminal of the amplifier. Both the first and second RF filter stages include high-order RF filters.

According to still another aspect of the present invention, an RF receiver includes a first RF filter, a second RF filter coupled to the first RF filter, an amplifier coupled to the second RF filter, a third RF filter coupled to the amplifier, and a fourth RF filter coupled to the third RF filter.

The first through fourth RF filters may include thin film superconducting elements. The first through fourth RF filters may be disposed on respective substrates or, alternatively, be disposed on first and second substrates. The first through fourth RF filters are preferably low order filters.

Other features and advantages are inherent in the RF receiver configurations claimed and disclosed or will become apparent to those skilled in the art from the following detailed description in conjunction with the accompanying drawings.

DETAILED DESCRIPTION OF THE PREFERRED EMBODIMENT

The present invention provides RF bandpass filter-amplifier configurations having both high selectivity and a low noise figure (i.e., the ratio in dB of the output noise power to the input noise power scaled by any gain). In each configuration, the bandpass filtering is split into two RF filter stages separated by an amplifier stage. A filter (or amplifier) "stage", as used herein, shall be understood to denote a device having one or more filters (or amplifiers). The first RF filter stage protects the amplifier stage by rejecting out-of-band frequencies, while the second RF filter stage improves the selectivity. The amplifier stage should introduce as little noise into the system as possible, while also providing a mechanism for isolating the two RF filter stages. The isolation permits the two RF filter stages to be tuned separately. As a result, two RF filter stages may provide the extraordinary rejection of a single, ultra-high-order RF filter without the impracticalities of manufacturing and tuning such an ultra-high-order RF filter. The intervening amplifier stage also renders the noise added by the second RF filter stage relatively inconsequential, thereby permitting the use of less expensive, conventional RF filters.

Figure 1:
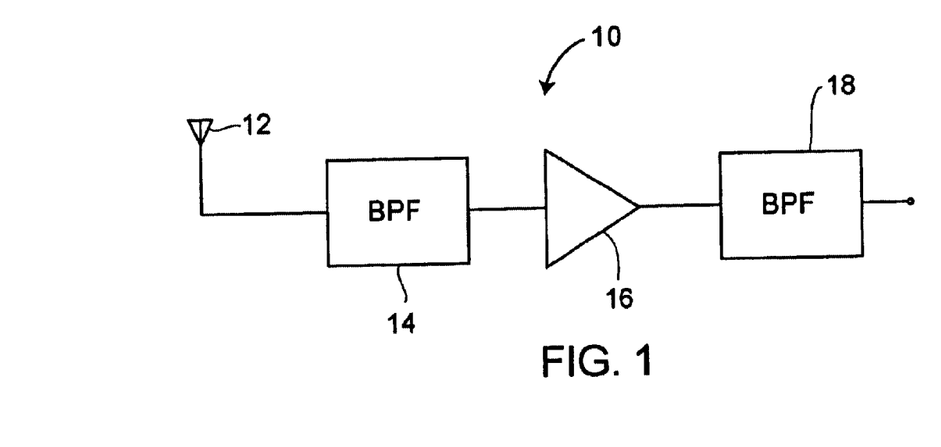
FIG. 1 is a block diagram of an RF filter-amplifier configuration in accordance with one embodiment of the present invention.

With reference to FIG. 1, an RF communication system receiver generally indicated at 10 includes an antenna 12 coupled to an RF bandpass filter stage 14, which has an output terminal coupled to an input terminal of an amplifier stage 16. The RF receiver 10 may be incorporated into a cellular telephone base station or, more generally, any component of a communication system that receives RF signals. The components of the RF receiver 10 may be coupled together by 50 Ohm coaxial cables or any other suitable transmission line known to those skilled in the art. Of course, to avoid reflection and, therefore, signal loss, the transmission line should have an impedance matching the input and output impedances of the elements of the RF receiver 10.

The amplifier stage 16 may include one or more amplifiers (not shown), each of which is preferably a low-noise amplifier (LNA). For example, the amplifier stage 16 may utilize an LNA available from JCA Technology (Camarillo, Calif.) as product number JC12-2342D. Such an LNA provides about 25 dB of gain over the frequency range 1850 to 1910 MHz with a maximum noise figure of about 1.2 dB at room temperature. Alternatively, the amplifier stage 16 includes a lower frequency LNA available from JCA Technology as product number JCA01-3140, which provides similar performance specifications over the frequency range 824 to 849 MHz.

In accordance with the present invention, an output terminal of the amplifier stage 16 is coupled to an input terminal of another RF bandpass filter stage 18. The two RF filter stages 14 and 18 may include one or more distinct passive RF filters. Each RF filter, in turn, may include a plurality of resonant elements for attenuating signals of undesired frequencies. The resonant elements may constitute resonant cavities, thin film structures on dielectric substrates, or any other resonant structure known to those skilled in the art to be suitable for RF signals. These resonant elements may form quasi-elliptic, elliptic, Tchebycheff, or Butterworth filters.

The resonant elements of the RF filter stages 14 and 18 may utilize HTSC materials, conventional (i.e., non-HTSC) materials, or both. Thus, the RF filter stage 14 may, for example, include a single thin film, HTSC filter, while the RF filter stage 18 includes a pair of cascaded, conventional, resonant cavity filters. In another exemplary embodiment, both of the RF filter stages 14 and 18 include a single conventional, resonant cavity filter.

The RF filter stages 14 and 18 are preferably not identical. Because the RF filter stage 14 precedes any amplification of the incoming signal, any filters in the RF filter stage 14 preferably have a low insertion loss. For example, the HTSC filters described hereinbelow provide excellent rejection characteristics with very low losses and, thus, may be incorporated into the RF filter stage 14. In contrast, the RF filter stage 18 may, but need not, include such low-loss filters. The gain of the intervening amplifier stage 16 scales down the insertion loss of the RF filter stage 18, such that the noise factor (i.e., the ratio of the output noise power to the input noise power) of this portion of the RF receiver 10 is as follows:

$$NF_{system} = NF_{stage_1} + NF_{stage_1}(NF_{amp} - 1) + \frac{(NF_{stage_2} - 1)NF_{stage_1}}{G}$$

where G is the gain factor of the amplifier stage 16 and $NF_{system}$, $NF_{stage1}$, $NF_{stage2}$, and $NF_{amp}$ are the noise factors for the RF receiver 10, the RF filter stage 14, the RF filter stage 18, and the amplifier stage 16, respectively. The gain of the amplifier stage 16 may be so significant (e.g., more than 15 dB) that a conventional RF filter may be utilized without any appreciable insertion loss. Assuming that the amplifier stage 16 utilizes an LNA, the system noise factor (or figure in dB) becomes almost entirely dependent on the insertion loss (i.e., the noise factor) of the RF filter stage 14 and the noise factor of the amplifier stage 16.

The two RF filter stages 14 and 18 may also provide different amounts of rejection. Different amounts of rejection may refer to rejection either near or far from the edges of the passband. Preferably, and unless stated otherwise, filters or filter stages will be compared herein in terms of their rejection just outside of the passband (e.g., a frequency at about ten percent more than the equivalent low pass filter bandwidth). In a preferred embodiment, the RF filter stage 14 includes a relatively low-order HTSC filter, while the RF filter stage 18 includes a high-order conventional filter. In this manner, the low-loss nature of the HTSC filter and the low noise figure of the amplifier stage 16 are determinative of the noise figure of the RF receiver 10, and the high-order conventional filter provides the bulk of the selectivity. In such an embodiment, significant cost savings are obtained due to the decreased reliance on HTSC materials —with hardly any appreciable difference in selectivity or sensitivity.

A "high-order filter," as used herein, shall be understood to refer to an RF filter having more than about ten poles, and preferably about sixteen or more poles, or an RF filter that provides, for instance, more than about 40 dB of rejection at a frequency about ten percent more than the equivalent low pass filter bandwidth. A "low-order filter" shall be understood to refer to an RF filter having less than about ten poles, or an RF filter that provides, for instance, less than about 20 dB of rejection at a frequency about ten percent more than the equivalent low pass filter bandwidth.

In operation, the amplifier stage 16 acts as an isolator for the cascaded RF filter stages 14 and 18. In order to minimize reflection and signal losses, directly cascaded filters must, of course, be impedance-matched. (Directly cascaded filters, as described herein, are filters coupled together without any intervening amplifier or buffer stage.) High-order filters, however, become extremely sensitive to component parameters, including the load impedance, and are not perfectly matched to even an ideal 50 Ohm load. This problem becomes particularly acute for RF filters having about sixteen or more poles. Thus, even an additional slight impedance mismatch may result in the de-tuning of directly cascaded filters. In contrast, low-order filters are usually well matched to an ideal 50 Ohm load. As a result, re-tuning such low-order filters is usually not necessary. It is for these reasons that the RF filter stages 14 and 18 are separated by the amplifier stage 16 in accordance with the present invention, but the individual RF filter(s) within each RF filter stage 14, 18 need not be separated. In such multiple filter embodiments, the individual RF filters within a stage are preferably of a sufficiently low order to accommodate direct coupling to each other, while each RF filter stage 14 and 18 will operate as a high-order filter in the aggregate and, thus, not be directly cascaded.

Figure 2:
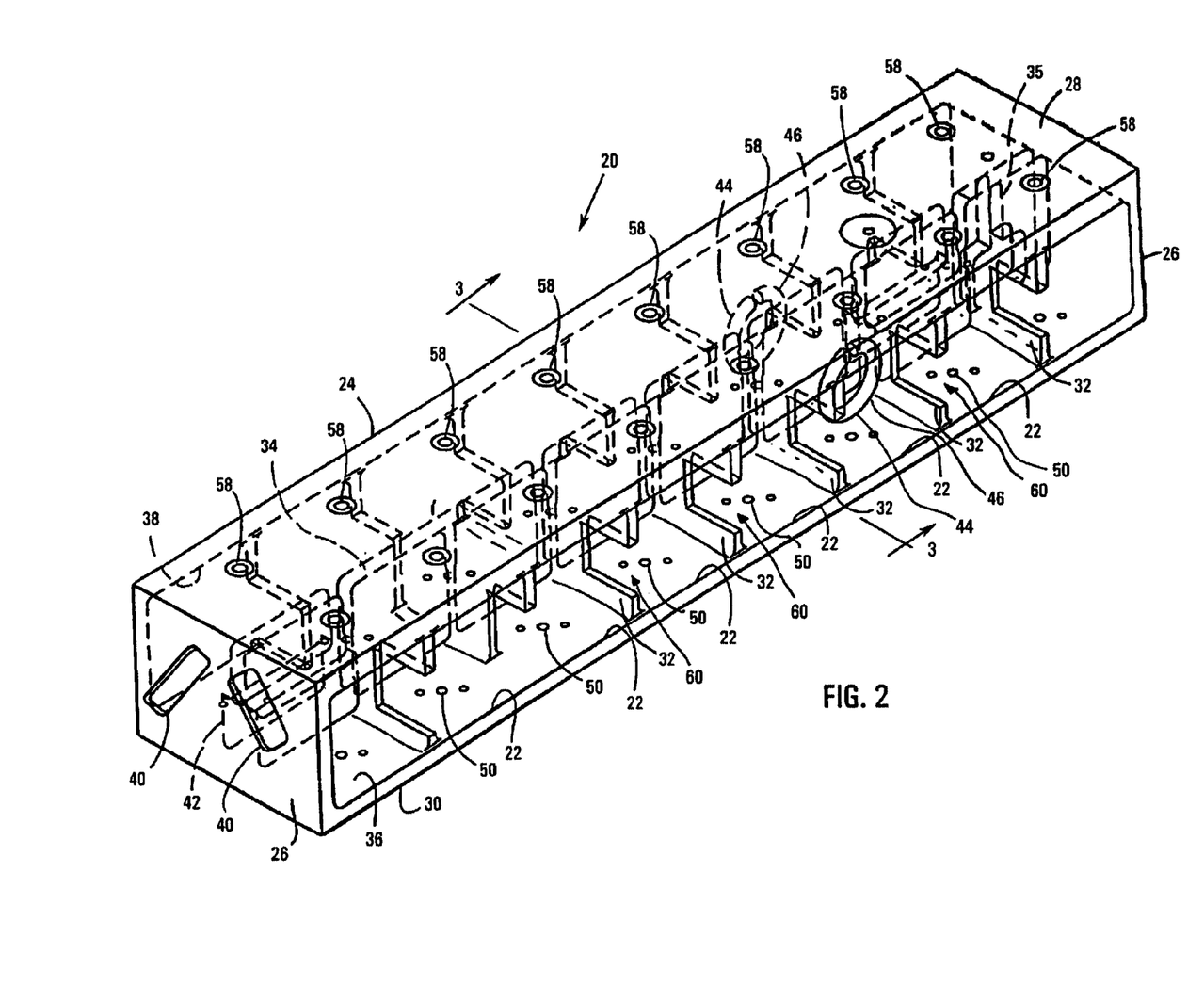
FIG. 2 is an isometric, partial view of a sixteen pole, resonant cavity filter for use in the RF filter-amplifier configuration of FIG. 1.
Figure 3:
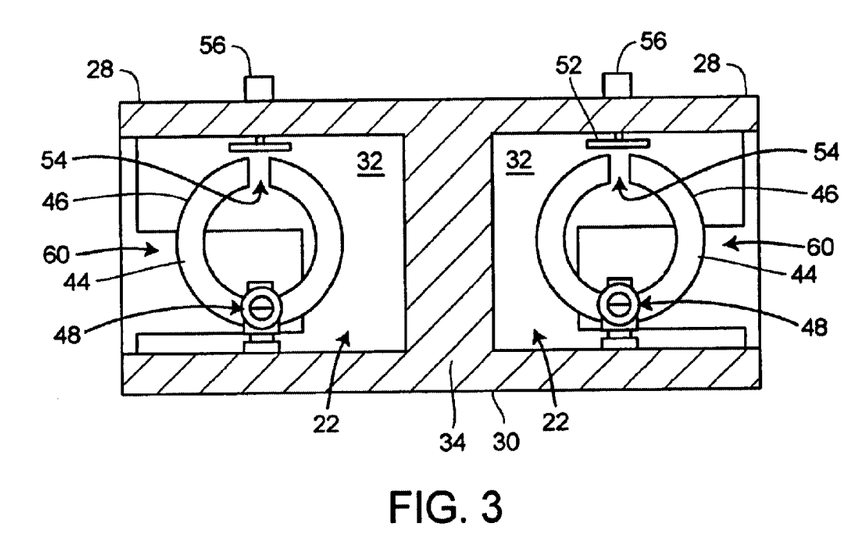
FIG. 3 is a cross-sectional view of the resonant cavity filter of FIG. 2 taken along the lines 3—3.

With reference to FIGS. 2 and 3, either the RF filter stage 14 (FIG. 1), the RF filter stage 18 (FIG. 1), or both, may include an RF filter generally indicated at 20 (FIG. 2) having multiple resonant cavities 22. The resonant cavities 22 of the RF filter 20 are defined by a housing 24 having a pair of end walls 26 (FIG. 2), an upper wall 28, and a lower wall 30. The housing 24 also includes a pair of plates (not shown) that are secured via screws or the like to the end walls 26, the upper wall 28, and the lower wall 30. The housing 24 also includes multiple inner walls 32 for separating adjacent resonant cavities 22. As shown, the RF filter 20 may include multiple rows of resonant cavities 22 separated by an inner partition wall 34. In such an instance, the inner partition wall 34 has a coupling aperture 35 (FIG. 2) formed therein for coupling together the rows of resonant cavities 22.

The thickness of the inner partition wall 34 may vary to accommodate different coupling requirements. For example, the housing has an input cavity 36 (FIG. 2) and an output cavity 38 (FIG. 2) having respective apertures 40 (FIG. 2) for insertion of a coupling mechanism (not shown). The input and output cavities 36, 38 are separated by a portion 42 (FIG. 2) of the inner partition wall 34 having approximately twice the thickness of the majority of the inner partition wall 34. The portion 42 of the inner partition wall 34 is provided in light of frequency and loading considerations known by those skilled in the art.

The input and output coupling mechanisms are, in turn, connected to respective RF transmission lines that carry the input and output RF signals. In general, each coupling mechanism includes an antenna (not shown) for propagating (or collecting) electromagnetic waves within the input and output cavities 36 and 38. The antenna may include a simple conductive loop or a more complex structure that provides for mechanical adjustment of the position of a conductive element within the cavity 36, 38. An example of such a coupling mechanism is described in U.S. Pat. No. 5,731,269, the disclosure of which is hereby incorporated by reference.

Each resonant cavity 22 includes a resonant element 44, which preferably, in turn, includes a split-ring, toroidal resonator 46. The resonator 46 may be oriented within the resonant cavity 22 in the manner shown in FIGS. 2 and 3 to achieve a certain degree and type of coupling, or otherwise as is known to those skilled in the art. Each resonator 46 may be secured to the lower wall 30 by a dielectric mounting mechanism generally indicated at 48 (FIG. 3). The mounting mechanism 48 may be secured to the lower wall 30 via screws (not shown) or the like that extend through apertures 50 (FIG. 2). Further details on exemplary mounting mechanisms may be found in U.S. patent application Ser. No. 08/556,371, the disclosure of which is hereby incorporated by reference. Another suitable dielectric mounting mechanism is described and shown in U.S. patent application Ser. No. 08/869,399, the disclosure of which is also hereby incorporated by reference.

The tuning of each resonant cavity 22 is primarily adjusted by a tuning disk 52 (FIG. 3) that projects into the resonant cavity 22 near a gap 54 (best seen in FIG. 3) in the resonator 46. Each tuning disk 52 is coupled to a screw assembly 56 (FIG. 3) that extends through an aperture 58 (FIG. 2) in the upper wall 28. Such a mechanism for tuning split-ring resonators is well known to those skilled in the art and will not be further described herein. Further details, however, may be found in the disclosure of U.S. patent application Ser. No. 08/556,371.

With continued reference to FIGS. 2 and 3, adjacent resonant cavities 22 of the RF filter 20 are coupled via a coupling aperture 60 in each inner wall 32. The size and shape of the coupling aperture 60 may vary greatly, as will be appreciated by those skilled in the art. For instance, as shown in FIG. 3, the coupling aperture 60 may generally be T-shaped. In contrast, as shown in FIG. 2, other adjacent resonant cavities 22 may be coupled together by larger and differently shaped apertures. For example, it should be noted that the coupling aperture 35 has a significantly different shape than the other coupling apertures 60.

Adjustment of the coupling between resonant cavities 22 to further tune the RF filter 20 and establish a particular response curve is accomplished via coupling screws (not shown) disposed in apertures (not shown) in the upper wall 28. The apertures are preferably positioned such that each coupling screw projects into a respective coupling aperture 60.

The housing 24 of the RF filter 20 is preferably made of silver-coated aluminum, but may be made of a variety of materials having a low resistivity. Similarly, the split-ring resonators 46 may be made of a low resistance metal and, in one embodiment of the present invention, be coated with an HTSC material. Further details on the chemical composition and method for manufacturing such HTSC materials may be found in U.S. patent application Ser. No. 08/794,038 (issuing as U.S. Pat. No. 5,789,347), the disclosure of which is hereby incorporated by reference.

In one embodiment of the present invention, the selectivity of an ultra-high-order (e.g., about twenty-eight poles), quasi-elliptic filter is provided by cascading two of the above-described sixteen pole, resonant cavity filters. With each filter representing one of the RF filter stages 14 and 18, respectively, the two filters are coupled together by the above-described, higher frequency LNA commercially available from JCA Technology. The sixteen pole filters are immensely easier to manufacture and tune relative to the alternative twenty-eight pole filter. In general, such ultra-high-order filters have about twenty-six or more poles, such that rejection of about 100 dB or more may be provided near the passband edge (or at a frequency about ten percent more than the equivalent low pass filter bandwidth).

More particularly, each sixteen pole filter provides a quasi-elliptic response and has one cross-coupling, such that the response of each filter has only one zero (i.e., a frequency at which the transfer function of a filter approaches negative infinity in dB). The cross-coupling between resonant cavities 22 may be implemented by a mechanism (such as an aperture between two cavities) well known to those skilled in the art to achieve electric (i.e., negative) coupling.

The two filters need not be tuned such that their respective response curves are identical. In fact, to improve rejection by providing more degrees of freedom to the RF receiver designer, the respective zeros of each filter are preferably non-coinciding. In this manner, when the RF filter stages 14 and 18 are cascaded, the transfer functions of the RF filter stages 14 and 18 are multiplied, and the resulting system response is improved by having two distinct zeros. In one example, both filters may be tuned to have a center frequency of 1950 MHz, with the first filter having a 3 dB bandwidth of 15.20 MHz and the second filter having a bandwidth of 15.18 MHz. The two filters and the LNA are coupled together by 50 Ohm coaxial cables.

With each filter comprising HTSC resonant elements, the first filter individually provides a rejection of approximately 55 dB at 1958.1 MHz, while the second filter individually provides 40 dB of rejection at the same frequency. When the filters are cascaded in accordance with the present invention, more than 90 dB of rejection is provided at that frequency. Near the edge of the passband, however, the noise figure of the system will correspond with only approximately the losses introduced by the first filter and the noise introduced by the LNA.

In another embodiment utilizing cavity resonators, both of the RF filter stages 14 and 18 consist of a ten-pole, quasi-elliptic RF filter, having HTSC resonant elements and two cross-couplings. The ten-pole HTSC filters are commercially available as "PCS" filters from the assignee of the present application, Illinois Superconductor Corporation (Mt. Prospect, Ill.). As will be appreciated by those skilled in the art, the two cross-couplings improve the rejection at frequencies near the passband edge, at the expense of sacrificing some rejection further away. Individually, each PCS filter was tuned to a center frequency of 1855.315 MHz with a bandwidth of approximately 13.9 MHz. Once again, the above-described, higher frequency LNA was utilized for the intervening amplifier stage 16.

Each PCS filter individually provides an approximate rejection of 54 dB at 1846.9 and 1863.9 MHz. Cascading the filters in accordance with the present invention improved rejection to over 100 dB at those same frequencies without any detrimental effect on the system noise figure. With the amplifier stage 16 providing about 29 dB of gain, the system noise figure remained at approximately the same level as a system having only the RF filter stage 14 and the amplifier stage 16 (about 0.5 dB). Lastly, it should be noted that, as in the previous embodiment, the filters were designed such that the respective zeros were non-coinciding, which improved the rejection.

As set forth above, the present invention is not limited to use with filters having superconducting resonant elements. Nor is the present invention limited to RF filter-amplifier configurations having RF filters that provide relatively the same amount of rejection. Indeed, in a preferred embodiment, the system noise figure of the RF receiver 10 is established by a low-loss, low-order RF filter preceding the amplifier stage 16 and the noise figure of the LNA. The low-order RF filter may only provide sufficient selectivity to protect the amplifier stage 16 from amplifying signals of undesired frequencies. The bulk of the rejection may be accomplished by a high-order RF filter coupled to the output terminal of the amplifier stage 16. An example of an RF receiver having such a filter-amplifier configuration is set forth below.

According to yet another embodiment utilizing resonant cavity filters, the RF filter stage 14 consisted of a quasi-elliptic, ten-pole HTSC filter with three cross-couplings, while the RF filter stage 18 consisted of an eleven pole, conventional filter available from Bartley Machining and Manufacturing Corp. (Amesbury, Mass.), as product number 847311024. The amplifier stage 16 consisted of the above-described, lower frequency JCA filter. Both RF filters were separately tuned to have a center frequency of 842 MHz and a bandwidth of approximately 15 MHz, which corresponds with the U.S. Cellular B-band.

Alone the HTSC filter provided 58 dB of rejection at 3 MHz away from the band edge (about 852 dB). The cascaded filter-amplifier configuration of the present invention, however, provided more than 110 dB. This improvement in selectivity was accomplished while maintaining a noise figure below 1 dB, despite the use of a conventional filter. Thus, the present invention provides an RF filter-amplifier configuration having both excellent selectivity and sensitivity, with a significant reduction in cost due to the decreased reliance on HTSC resonators.

In yet another embodiment, further cost reductions may be obtained with both of the RF filter stages 14 and 18 consisting of conventional RF filters. As in the previous embodiments, the noise figure for the entire RF receiver 10 will be predominantly determined by the insertion loss of the RF filter stage 14 and the noise figure of the amplifier stage 16. Thus, as long as conventional RF filters having a relatively high Q are utilized in the RF filter stage 14, the noise figure for the entire RF receiver 10 may be quite low—despite the use of an inexpensive conventional RF filter in the RF filter stage 18.

The present invention is not limited to use with cavity resonator filters. For instance, the RF filter stages 14 and 18 may alternatively include RF filters relying on thin film superconductor resonators. Thin film resonators provide the potential for significant size reductions. Accordingly, past RF filters utilizing thin film resonators have tended to include a single wafer having as many as stages disposed thereon as possible. This approach has led to high power densities and, eventually, intermodulation distortion. Despite these design problems, single chip integration has remained the standard approach. In contrast, the present invention may be utilized in the thin film context to alleviate the power density problem, while concurrently providing improved rejection.

Figure 4:
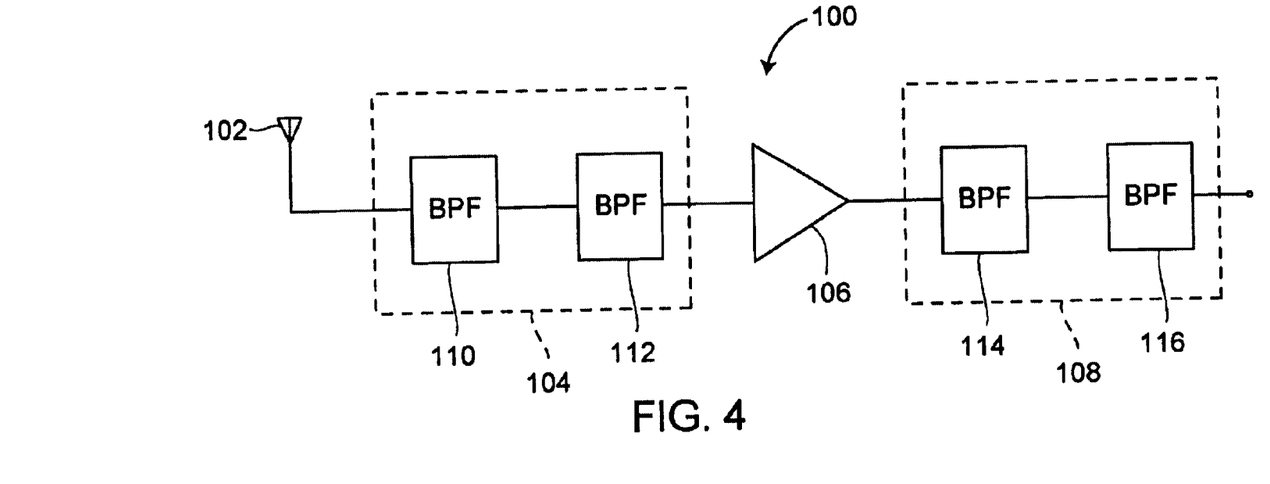
FIG. 4 is a block diagram of an RF filter-amplifier configuration in accordance with another embodiment of the present invention.

With reference now to FIG. 4, an alternative RF receiver indicated generally at 100 includes an antenna 102, a first RF filter stage 104, an amplifier stage 106 similar to the amplifier stage 16, and a second RF filter stage 108. In one embodiment, the first RF filter stage 104 includes a pair of cascaded RF bandpass filters 110 and 112, while the second RF filter stage also includes a pair of cascaded RF bandpass filters 114 and 116. Because the pairs of bandpass filters 110, 112, 114, 116 are directly cascaded, each RF filter is preferably a low order filter. In this manner, the direct cascading of the filters will not result in any detrimental loading effects.

The amplifier stage 106, however, allows the benefits of the two filter stages 104 and 108 to be combined. More particularly, if the individual filters 110, 112, 114, 116 are, for example, six to eight pole filters, the RF filter stages 104 and 108 would interact detrimentally without the intervening amplifier stage 106 serving as an isolator.

Figure 5:
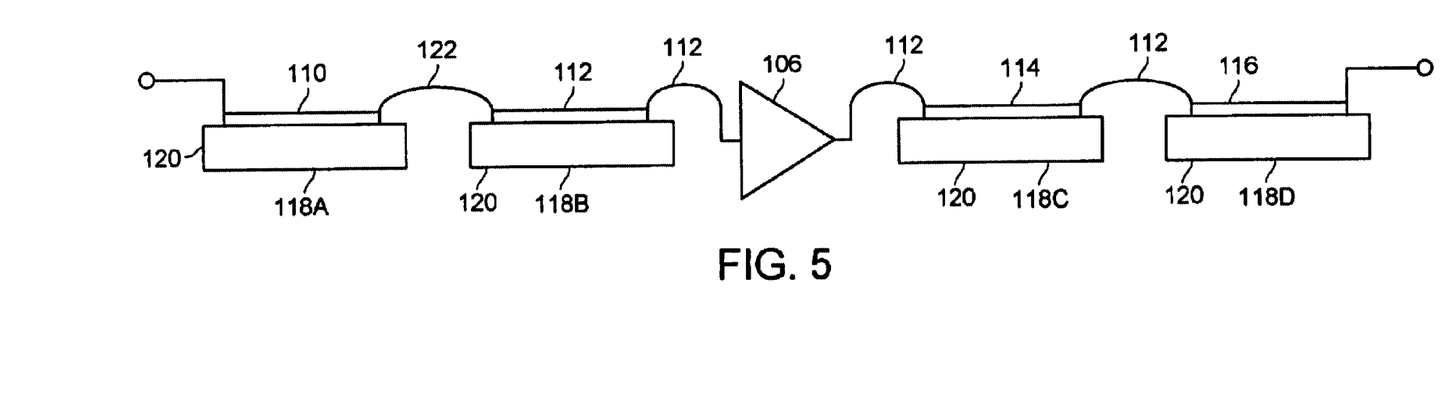
FIG. 5 is a schematic diagram of one embodiment of the RF filter-amplifier configuration of FIG. 4 utilizing thin film HTSC resonant elements.

Referring now to FIG. 5, the thin film filters 110, 112, 114, 116 may be spread over four dielectric chips 118A, 118B, 118C, 118D, respectively. Disposing each respective filter on a corresponding separate chip will provide more space, thereby alleviating the power density problem. Each chip includes a dielectric substrate 120 and suitable bonding wires schematically indicated at 122. The bonding wires 122 of the RF filters 112 and 114 are coupled to the amplifier stage 106 which may or may not be disposed on a separate chip. Alternatively, the RF filters of the first RF filter stage 104 may be disposed on a first substrate, while the RF filters of the second RF filter stage 108 are disposed on a second substrate.

The foregoing detailed description has been given for clearness of understanding only, and no unnecessary limitations should be understood therefrom, as modifications would be obvious to those skilled in the art.

What is claimed is:

1. An RF receiver comprising:
   a first RF filter stage having an output terminal;
   an amplifier having an input terminal and an output terminal wherein the input terminal is coupled to the output terminal of the first RF filter stage; and
   a second RF filter stage having an input terminal coupled to the output terminal of the amplifier;
   wherein the first RF filter stage and the second RF filter stage have approximately the same center frequencies and bandwidths and comprise a respective bandpass filter such that highly selective bandpass filtering is achieved via the first RF filter stage and the second RF filter stage, and wherein the second RF filter stage comprises a first plurality of superconducting resonant elements.

2. The RF receiver of claim 1, wherein the second RF filter stage provides more rejection than the first RF filter stage.

3. The RF receiver of claim 2, wherein the amplifier comprises a low noise amplifier.

4. The RF receiver of claim 2, wherein the first RF filter stage comprises a low loss RF filter.

5. The RF receiver of claim 4, wherein the bandpass filter of the first RF filter stage has a higher insertion loss than the low loss RF filter.

6. The RF receiver of claim 5, wherein the second RF filter stage comprises a second plurality of conventional resonant elements.

7. The RF receiver of claim 1, wherein the first RF filter stage and the second RF filter stage comprise a respective plurality of thin film superconductor resonators.

8. The RF receiver of claim 1, wherein:
   the first RF filter stage comprises a first RF filter and a second RF filter;
   the second RF filter stage comprises a third RF filter and a fourth RF filter;
   the first RF filter is coupled to the second RF filter; and
   the third RF filter is coupled to the fourth RF filter.

9. The RF receiver of claim 8, wherein:
   each RF filter of the first through fourth RF filters comprises a respective plurality of thin film superconductor resonators; and
   each respective plurality of thin film superconductor resonators is disposed on a corresponding substrate.

10. The RF receiver of claim 1, wherein the first RF filter stage and the second RF filter stage comprise a respective high-order RF filter.

11. The RF receiver of claim 10, wherein the first RF filter stage and the second RF filter stage comprise respective superconducting resonant elements.

12. The RF receiver of claim 1, wherein the first RF filter stage comprises a superconducting resonant element and the second RF filter stage comprises a conventional resonant element.

13. An RF receiver comprising:
   a first RF filter stage having an output terminal;
   an amplifier having an input terminal and an output terminal wherein the input terminal is coupled to the output terminal of the first RF filter stage; and
   a second RF filter stage having an input terminal coupled to the output terminal of the amplifier;
   wherein the first RF filter stage and the second RF filter stage have approximately the same center frequencies and bandwidths and comprise a respective bandpass filter such that highly selective bandpass filtering is achieved via the first RF filter stage and the second RF filter stage,
   the bandpass filter of the first RF filter stage comprises a low loss RF filter, and
   the bandpass filter of the second RF filter stage provides more rejection than the first RF filter stage.

14. The RF receiver of claim 13, wherein the first RF filter stage and the second RF filter stage comprise respective superconducting elements.

15. The RF receiver of claim 13, wherein the second RF filter stage has a higher insertion loss than the low loss RF filter.

16. The RF receiver of claim 13, wherein the amplifier comprises a low noise amplifier.

17. The RF receiver of claim 13, wherein the first RF filter stage comprises a superconducting resonant element and the second RF filter stage comprises a conventional resonant element.

18. An RF receiver comprising:
   a first RF filter stage comprising superconducting material and having an output terminal;
   an amplifier having an input terminal and an output terminal wherein the input terminal is coupled to the output terminal of the first RF filter stage; and
   a second RF filter stage comprising superconducting material and having an input terminal coupled to the output terminal of the amplifier;
   wherein the RF first filter stage and the second RF filter stage comprise high-order RF filters.

19. The RF receiver of claim 18, wherein the first RF filter stage and the second RF filter stage have different response zeros.

20. The RF receiver of claim 18, wherein the second RF filter stage provides more rejection than the first RF filter stage.

21. The RF receiver of claim 18, wherein the amplifier comprises a low noise amplifier.

22. The RF receiver of claim 18, wherein the first RF filter stage and the second RF filter stage comprise a respective bandpass filter such that highly selective bandpass filtering is achieved via the first RF filter stage and the second RF filter stage.

23. An RF receiver comprising:
   a first RF filter;
   a second RF filter coupled to the first RF filter;
   an amplifier coupled to the second RF filter;
   a third RF filter coupled to the amplifier; and
   a fourth RF filter coupled to the third RF filter,
   wherein the first RF filter, the second RF filter, the third RF filter, and the fourth RF filter have approximately the same center frequencies and bandwidths and comprise a bandpass filter, respectively.

24. The RF receiver of claim 23, wherein each of the first through fourth RF filters comprises a respective thin film superconducting element.

25. The RF receiver of claim 24, wherein each of the first through fourth RF filters is disposed on a respective substrate.

26. The RF receiver of claim 24, wherein the first RF filter and the second RF filter are disposed on a first substrate and the third RF filter and the fourth RF filter are disposed on a second substrate.

27. The RF receiver of claim 23, wherein each of the first through fourth RF filters comprises a respective low-order RF filter.

28. The RF receiver of claim 23, wherein:
the first RF filter and the second RF filter provide a first collective selectivity;
the third RF filter and the fourth RF filter provide a second collective selectivity;
the second collective selectivity is greater than the first collective selectivity.

29. The RF receiver of claim 23, wherein highly selective bandpass filtering is achieved via the first RF filter, the second RF filter, the third RF filter, and the fourth RF filter.

30. An RF receiver comprising:
a first RF filter stage comprising superconducting material and having an output terminal;
an isolator having an input terminal and an output terminal wherein the input terminal is coupled to the output terminal of the first RF filter stage; and
a second RF filter stage having an input terminal coupled to the output terminal of the isolator;
wherein at least one of the first RF filter stage and the second RF filter stage comprises a high-order filter.

31. The RF receiver of claim 30, wherein the isolator comprises an amplifier.

32. The RF receiver of claim 30, wherein the first RF filter stage and the second RF filter stage have different response zeros.

33. The RF receiver of claim 30, wherein the first RF filter stage and the second RF filter stage have different selectivities.

34. The RF receiver of claim 30, wherein the first RF filter stage and the second RF filter stage comprise a respective bandpass filter such that highly selective bandpass filtering is achieved via the first RF filter stage and the second RF filter stage.

* * * * *